US008371306B2

(12) United States Patent
Haines et al.

(10) Patent No.: US 8,371,306 B2
(45) Date of Patent: *Feb. 12, 2013

(54) SURGICAL DRAPE AND SYSTEM HAVING A BARRIER FOR PREVENTING THE START OF A SURGICAL PROCEDURE AND METHODS FOR USING SAME (75) Inventors: Kimberly M. Haines, Deerfield, IL (US); Robert A. Lockwood, Libertyville, IL (US); Francis A. Czajka, Libertyville, IL (US)

(73) Assignee: Medline Industries, Inc., Mundelein, IL (US)

( * ) Notice: Subject to any disclaimer, the term of this patent is extended or adjusted under 35 U.S.C. 154(b) by 62 days.

This patent is subject to a terminal disclaimer.

(21) Appl. No.: 12/985,076

(22) Filed: Jan. 5, 2011

(65) Prior Publication Data
US 2011/0094521 A1  Apr. 28, 2011

Related U.S. Application Data (62) Division of application No. 12/008,818, filed on Jan. 14, 2008, now Pat. No. 7,886,742.

(51) Int. Cl.
*A61G 15/00* (2006.01)
*A47B 71/00* (2006.01)
*A47B 7/00* (2006.01)
(52) U.S. Cl. ................... 128/845; 5/613; 5/600
(58) Field of Classification Search .......... 128/846, 128/849, 853, 854
See application file for complete search history.

(56) References Cited

U.S. PATENT DOCUMENTS

| 3,800,790 A | * | 4/1974 | Collins | 128/854 |
| 3,826,253 A | | 7/1974 | Larsh et al. | 128/132 D |
| 4,857,713 A | | 8/1989 | Brown | 235/375 |
| 4,947,867 A | | 8/1990 | Keeton | 128/846 |
| 5,197,493 A | * | 3/1993 | Grier-Idris | 128/853 |
| 5,445,165 A | * | 8/1995 | Fenwick | 128/849 |
| 5,979,450 A | | 11/1999 | Baker et al. | 128/849 |
| 6,382,212 B1 | * | 5/2002 | Borchard | 128/849 |
| 6,955,002 B2 | | 10/2005 | Sandel et al. | 40/638 |
| 2002/0179094 A1 | | 12/2002 | Perlow | 128/897 |
| 2003/0182815 A1 | | 10/2003 | Carlson, II | 33/566 |

(Continued)

FOREIGN PATENT DOCUMENTS
WO WO 03/082136 A1 1/2003

OTHER PUBLICATIONS

The Joint Commission, 2008 National Patient Safety Goals Manual, pp. 1-19, available on Jun. 25, 2007.

(Continued)

*Primary Examiner* — Loan Thanh
*Assistant Examiner* — Tarla Patel
(74) *Attorney, Agent, or Firm* — Nixon Peabody LLP (57) ABSTRACT A surgical drape, system and method of using comprise a surgical drape having a fenestration to be placed over a surgical site of a patient. The surgical drape includes a barrier removably attached to the surgical drape and adapted for placement over a portion of the fenestration to prevent the start of the surgical procedure. Upon verification of a set of predetermined conditions, the barrier is removed by a member of the surgical staff in order to begin the surgical procedure.

20 Claims, 6 Drawing Sheets

U.S. PATENT DOCUMENTS

| | | | |
|---|---|---|---|
| 2003/0187458 A1* | 10/2003 | Carlson, II | 606/116 |
| 2004/0056477 A1 | 3/2004 | Bruce | 283/81 |
| 2004/0056478 A1 | 3/2004 | Bruce | 283/81 |
| 2005/0183182 A1 | 8/2005 | Keenan | 2/114 |
| 2005/0193609 A1 | 9/2005 | Schwartz | 40/638 |
| 2005/0211590 A1 | 9/2005 | McClure et al. | 206/438 |
| 2005/0268505 A1 | 12/2005 | Sandel et al. | 40/324 |
| 2006/0096877 A1 | 5/2006 | Khajavi et al. | 206/363 |
| 2007/0102005 A1 | 5/2007 | Bonutti | 128/849 |

OTHER PUBLICATIONS

Written Opinion corresponding to International Patent Application No. PCT/US2009/030684, European Patent Office, dated Apr. 14, 2009, 7 pages.

International Search Report corresponding to International Patent Application No. PCT/US2009/030684, European Patent Office, dated Apr. 14, 2008, 5 pages.

* cited by examiner

SURGICAL DRAPE AND SYSTEM HAVING A BARRIER FOR PREVENTING THE START OF A SURGICAL PROCEDURE AND METHODS FOR USING SAME

CLAIM OF PRIORITY AND CROSS-REFERENCE TO RELATED APPLICATION

This application is a divisional of U.S. patent application Ser. No. 12/008,818, which was filed on Jan. 14, 2008, and is incorporated herein by reference in its entirety.

TECHNICAL FIELD

The present disclosure relates generally to surgical drapes. More particularly, the present disclosure relates to surgical drapes having a barrier across a portion of a fenestration of the surgical drape to prevent a surgical team from beginning a surgical procedure without performing a verification of the correct person, procedure, site and side.

BACKGROUND

Healthcare facilities are increasingly concerned about the occurrence of errors in surgical procedures involving operating on the wrong patient, on the wrong surgical site, on the wrong side of the patient and even performing the wrong surgical procedure. As a result, more attention is being turned to the activities of the surgeon and operating staff prior to performing the surgery. A "time out" or surgical pause is often required by healthcare facilities in an effort to reduce or eliminate the occurrence of surgical errors. According to the "time out" procedure, a nurse or other operating staff member calls a "time out" in the operating room to call attention to a final safety check in an effort to ensure that the correct surgical procedure is going to be performed on the correct patient, the correct site and the correct side of the patient.

Some national organizations, such as The Joint Commission, have prepared a set of National Patient Safety Goals to promote specific improvements in patient safety. Specifically, this group has developed "Universal Protocols" for preventing wrong site, wrong procedure and wrong person surgeries. However, such protocols are not always followed by hospital staff. Some surgeons and operating room staff resist the safety checks by performing only a portion of the protocol or ignoring the protocol completely.

Therefore, there exists a need to provide a physical barrier to prevent the start of a surgical procedure until a predetermined verification procedure is completed. The benefit of providing a physical barrier in combination with a verification procedure is to make certain that the operation performed is correct. In addition to eliminating surgical errors, this also ensures that the operating team understands their role and that the patient has been properly prepared for the operation.

SUMMARY

According to one embodiment of the present disclosure, a surgical drape system for use in a surgical procedure comprises a surgical drape having a fenestration to be placed over a surgical site of a patient and a barrier removably attached to the surgical drape. The barrier is adapted for placement over a portion of the fenestration to prevent the start of the surgical procedure.

In another embodiment of the present disclosure, a method for using a surgical drape system comprises providing a surgical drape having a fenestration to be placed over a surgical site on a patient. The surgical drape includes a barrier removably attached to the surgical drape and extending over a portion of the fenestration to prevent the start of a surgical procedure. The method further comprises verifying a set of predetermined conditions prior to removing the barrier and removing the barrier prior to beginning the surgical procedure.

In yet another embodiment of the present disclosure, a surgical drape for use in a surgical procedure comprises a base having a top surface and a bottom surface, a fenestration located in a portion of the base for placing over a surgical site and a barrier attached to the base. The barrier is placed over a portion of the fenestration to prevent the start of the surgical procedure.

In a further embodiment of the present disclosure, a surgical drape system for use in a surgical procedure comprises a surgical drape having a fenestration to be placed over a surgical site of a patient, a barrier removably connected to the surgical drape and adapted for placement over a portion of the fenestration to prevent the start of the surgical procedure. The system further comprises an item removably attached to the barrier for displaying a predetermined verification procedure.

In a still further embodiment of the present disclosure, a method of providing a system for preventing surgical errors comprises the acts of providing a surgical drape having a fenestration adapted to be placed over a surgical site. The surgical drape includes a barrier across a portion of the fenestration to prevent the start of a surgical procedure. The method further comprises displaying a predetermined verification procedure, including one or more conditions, associated with the barrier and confirming the one or more conditions of the predetermined verification procedure.

In yet a further embodiment, a surgical drape system for use in a surgical procedure comprises a surgical drape for placement over a patient and at least one holder attached to the surgical drape. The holder holds an item associated with a predetermined verification procedure.

In yet a further embodiment, a surgical drape system for use in a surgical procedure comprises a surgical drape having a fenestration for placement over a patient and a fenestration cover for covering the fenestration. The fenestration cover is adapted to prevent the start of the surgical procedure.

The above summary of the present disclosure is not intended to represent each embodiment or every aspect of the present invention. The detailed description and figures will describe many of the embodiments and aspects of the present invention.

BRIEF DESCRIPTION OF THE DRAWINGS

The foregoing and other advantages of the invention will become apparent upon reading the following detailed description and upon reference to the drawings.

While the disclosure is susceptible to various modifications and alternative forms, specific embodiments have been shown by way of example in the drawings and will be described in detail herein. It should be understood, however, that the disclosure is not intended to be limited to the particular forms disclosed. Rather, the disclosure is to cover all modifications, equivalents, and alternatives falling within the spirit and scope of the disclosure.

DESCRIPTION OF ILLUSTRATIVE EMBODIMENTS

Figure 1A:
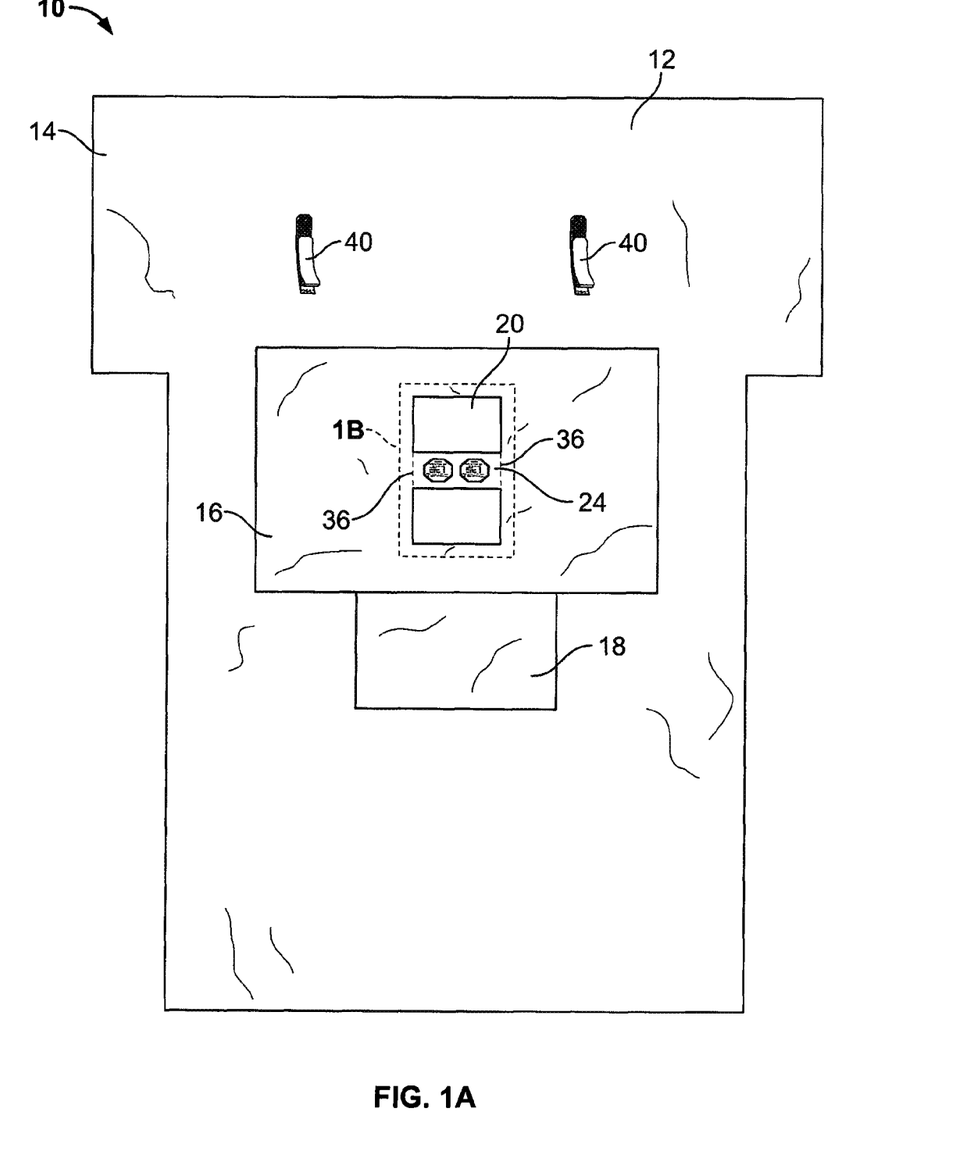
FIG. 1A is a top view of a surgical drape according to one embodiment of the present disclosure.
Figure 2:
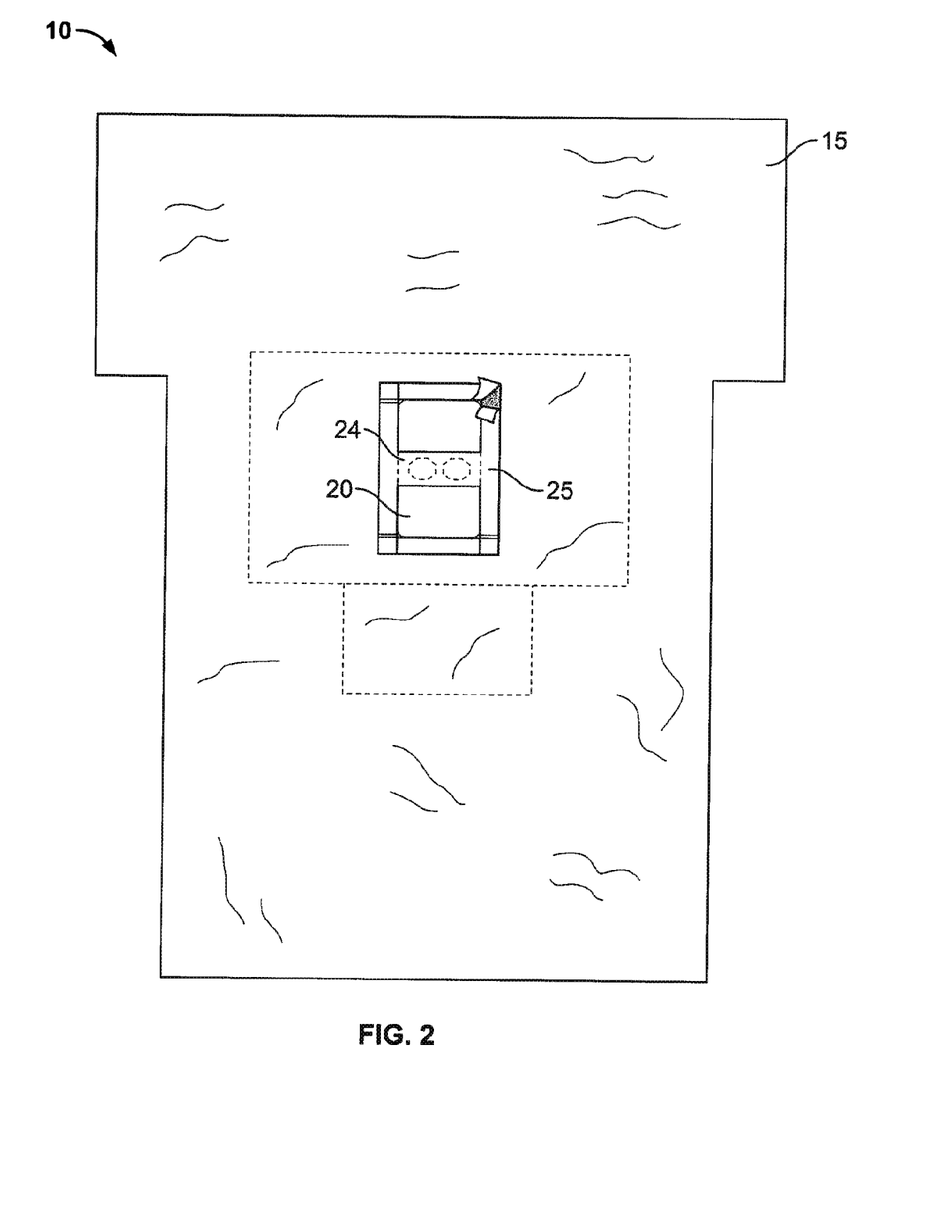
FIG. 2 is a bottom view of the surgical drape of FIG. 1.

FIG. 1A illustrates a surgical drape 10 including a base sheet 12 having a top surface 14 and a bottom surface 15 (see FIG. 2). The surgical drape 10 may include panels 16, 18. Panel 16 may be adapted for use as a reinforcement panel that absorbs blood and fluid from a surgical site. Panel 18 may be adapted for use as an anti-skid mat to prevent instruments from sliding on the drape 10. The surgical drape 10 also includes an opening or fenestration 20 for positioning over a surgical site. The fenestration 20 may be centrally located in the surgical drape 10 or may be positioned at other non-central locations in the surgical drape 10. As shown in FIG. 1A, the fenestration 20 is rectangular, but may include any other shapes that would be suitable for positioning over a surgical site. Also included on the surgical drape 10 may be one or more holders 40 which are described in more detail below.

As shown in FIG. 1A, positioned across the fenestration 20 is a barrier 24 for preventing the start of a surgical procedure. The barrier 24 may include a strip of material that is attached to the surgical drape 10 along a portion of the periphery of the fenestration 20. The barrier 24 may be made of any type of material that may be attached to a surgical drape 10, such as paper, cloth, polymeric materials, wax-covered paper, combinations thereof and any other material that would be suitable for attaching to the surgical drape 10.

Figure 3:
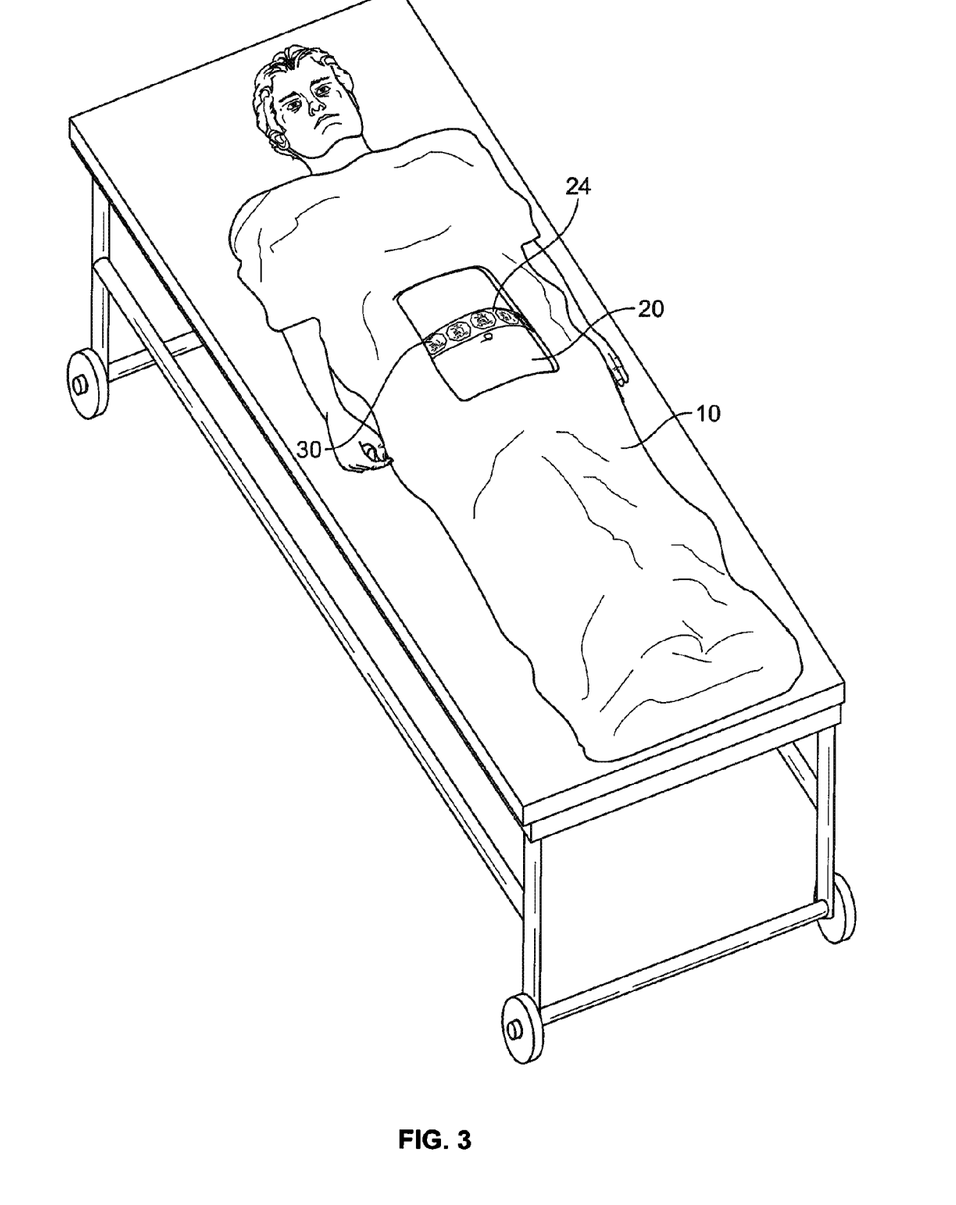
FIG. 3 is a perspective view of a surgical drape positioned over a patient according to another embodiment of the present disclosure.

In one embodiment, the barrier 24 may be attached to the bottom surface 15 of the surgical drape 10 shown in FIG. 2 via an adhesive material located around the periphery of the fenestration 20. The barrier 24 may be attached to the surgical drape 10 at two or more locations such that the barrier 24 is attached on one side of the fenestration 20 at a first location and is also attached on another side of the fenestration 20 at a second location directly opposite the first location. It is contemplated that the barrier 24 could be attached at other locations around the periphery of the fenestration 20. In the embodiments shown in FIGS. 1-3, the barrier 24 is attached at a first location on one side of the fenestration 20 and is attached at a second location on the opposite side of the fenestration 20 to form a barrier that extends across the fenestration. In addition to adhesives, the barrier 24 may be attached to the surgical drape 12 using hook and loop fasteners, e.g., Velcro®, string, loops, ties and other materials that would be suitable for attaching the barrier 24.

In some embodiments, attached to the adhesive material is one or more attachment strips 25, as shown in FIG. 2, that are removed when the surgical drape 10 is positioned on the patient. For a rectangular fenestration 24, the attachment strips 25 may be located on each side of the four sides of the fenestration 24. The barrier 24 may be attached to the surgical drape 10 such that the attachment strips 25 cover or overlay the portion of the barrier 24 that is attached to the surgical drape 10. In this scenario, the attachment strips 25 are attached to the adhesive material at locations other than where the barrier 24 is attached to the adhesive material.

As shown in FIGS. 1A through FIG. 3, the barrier 24 is positioned across the fenestration 20 to prevent the start of a surgical procedure until a predetermined verification procedure is completed. The predetermined verification procedure is designed to prevent the surgeon or other surgical staff from performing surgery on the wrong patient, as well as preventing them from performing the wrong surgical procedure, at the wrong surgical site or side of the patient. In effect, the surgeon and surgical staff are forced to perform a pause or "time out" before the surgical procedure begins. This pause allows the surgical staff to confirm the correct surgical patient, surgical procedure, and surgical site and side.

Figure 1B:
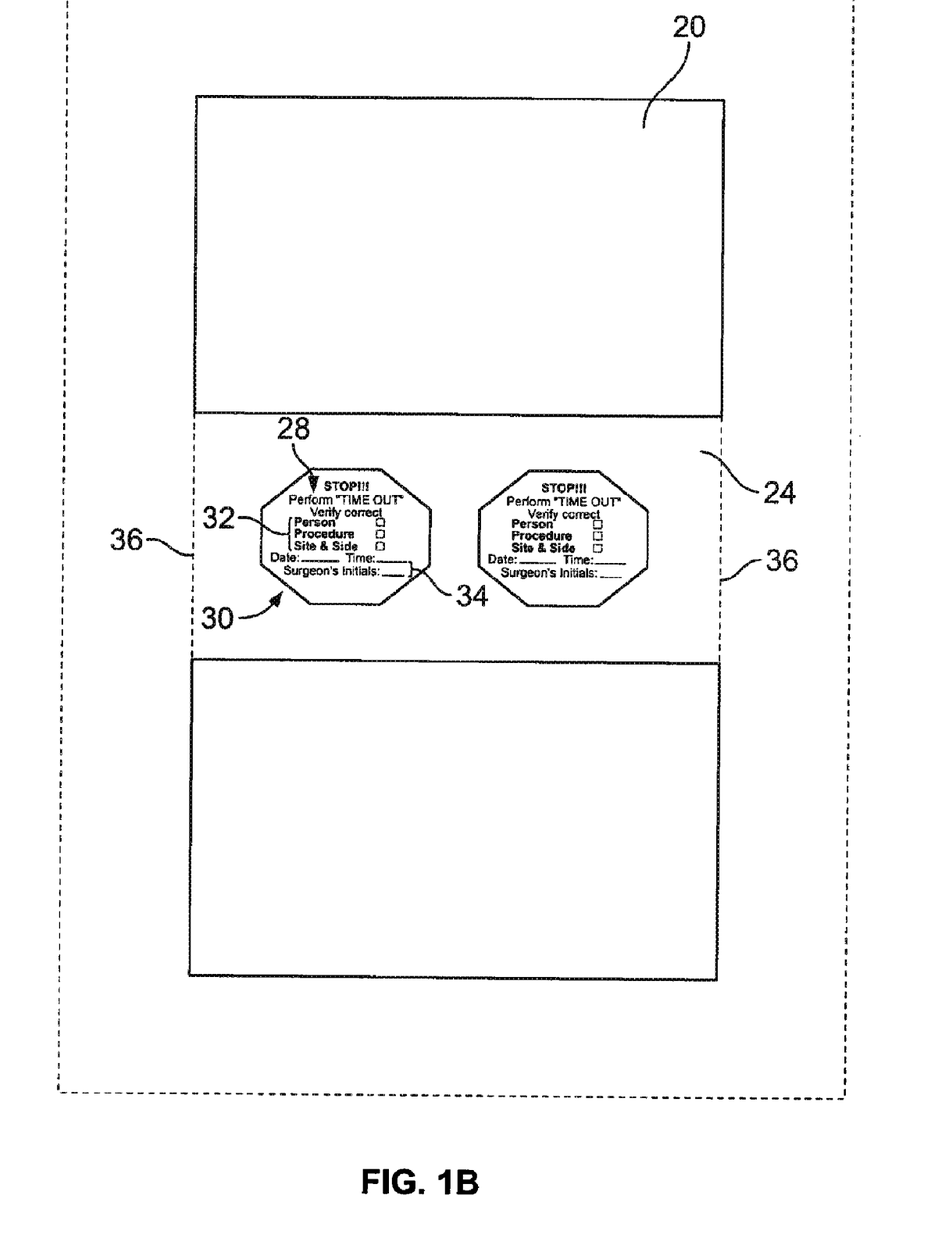
FIG. 1B is a front view of a fenestration of the surgical drape of FIG. 1 having a barrier located across a portion of the fenestration.

As shown in FIG. 1B, the elements of a predetermined verification procedure 28 may be displayed on an indicator or item 30 that may be attached to the barrier 24. According to one example of a predetermined verification procedure 28 shown on item 30 in FIG. 1B, the surgical staff is instructed to "STOP!! Perform 'TIME OUT' Verify Correct Person, Procedure, Site & Side." Thus, the surgical staff must stop, verify the correct person (by, for example, confirming the patient's name and date of birth), verify the correct procedure, verify the correct site and verify the correct side before the surgical procedure can begin. By prominently displaying the predetermined verification procedure 28 on the barrier 24, this ensures that the staff will not overlook the important steps that should be performed before the surgery begins. These steps will reduce the occurrences of "wrong patient," "wrong procedure," "wrong site" and "wrong side" surgeries. Surgical staff, hospitals and patients will benefit by the reduction or elimination of such occurrences.

The item 30 may contain a first area 32 for the surgical staff to indicate that each part of the verification procedure has been conducted by, for example, checking off a box for each part of the predetermined verification procedure 28 that is verified, i.e., the "Person," the "Procedure," and the "Site & Side." Additionally, the item 30 may include a second area 34 on the item 30 where a member of the surgical staff, such as the surgeon, can sign or initial, date and indicate the time that that the predetermined verification procedure 28 was conducted. The item 30 may include any shape that may be positioned on the barrier 24, such as an octagon as shown in FIG. 1B. The octagon may be used to resemble a "STOP" sign and will caution the surgical staff to pause before proceeding. Other shapes may include a circle, a square, a diamond, a triangle, a heart, a hexagon, a rectangle, an oval, a pentagon, and any other shapes that would be suitable for positioning on the barrier 24. The item 30 may also include a specific color, such as red, to draw the attention of the surgical staff to remind them of the need to complete the predetermined verification procedure 28.

The item 30 may comprise a label, a decal, a sticker, a stamp, an embossment, a tattoo, an ink or screen printed article, any combinations thereof and any other articles that have areas for displaying information to the surgical staff. The item 30 may be attachable to the barrier 24 and may be removed from the barrier 24 upon completion of the predetermined verification procedure 28. For example, the item 30 may have an adhesive material on one side of the decal, sticker, stamp, etc. that allows it to be removably attached to the barrier 24. Once removed from the barrier 28, the item 30 may be placed in the patient's medical records. In other embodiments, the predetermined verification procedure 28 may be printed or placed directly on the barrier 24 itself.

It is to be noted that the examples described herein and shown in FIG. 1B include four different elements to be verified (i.e., the person, the procedure, the site and the side); however, the predetermined verification procedure 28 may contain only one of these elements, a combination of these elements or additional elements that may be different from the elements shown in FIG. 1B. For example, the predetermined verification procedure 28 may also include verifying other elements, in addition to or as an alternative to those described above, such as verifying the correct position of the patient, the correct radiograph data (if needed), the availability of special equipment, implants and other requirements, any allergies the patient may have, any pre-operative antibiotics or medications that the patient is taking, any blood products that may be needed for transfusions prior to the surgical procedure or intraoperatively, the location of the family while at the hospital for communication purposes, and other elements that are relevant in a surgical setting.

After the predetermined verification procedure 28 is completed, and the item 30 is removed from the barrier 24 by a member of the surgical staff, the barrier 24 may be removed from the surgical drape 10 by the surgeon or other surgical staff member by tearing the barrier at one or more perforations located on the barrier 24. For example, as shown in FIGS. 1A and 1B, a set of perforations 36 is located at the edges of the fenestration 20 where it meets the surgical drape 24 such that the surgical staff can tear the barrier 24 relatively easily at both edges and remove the barrier 24 from the surgical drape 10.

The base 12 of the surgical drape 10 may be comprised of various materials such as polyethylene, polyester, cotton, paper, dexter, spunbond meltblown spunbond, microporous, foam, polypropylene, rayon, spunlace, trilaminate, bilaminate, combinations thereof and other suitable materials. The panel 16 may comprise impervious reinforcement material comprised of, for example, polypropylene. The panel 18 may comprise materials such as polyethylene, polyester, cotton, paper, dexter, spunbond meltblown spunbond, microporous, foam, polypropylene, rayon, spunlace, trilaminate, bilaminate, combinations thereof and other suitable materials. All of the materials used to make the base 12, the panels 16, 18, the barrier 24 and the item 30 must be sterilizable, such that the entire surgical drape 10 and barrier 24 may be used in a sterile environment, such as a hospital operating room. Once the surgical procedure is completed, the surgical drape 10 may be removed from the patient and discarded.

As discussed above, the barrier 24 prevents the start of a surgical procedure until the surgical staff performs the required "TIME-OUT" to verify the correct patient, the correct surgical procedure, the correct site and the correct side. Once all of these elements have been verified, the surgeon or other surgical staff member may remove the barrier 24 to begin the surgical procedure. One example of a predetermined verification procedure 28 as a way of preventing surgical errors is that developed by The Joint Commission's 2008 National Patient Safety Goal's "Universal Protocol." According to the Universal Protocol, a "time-out" is conducted in the location where the surgical procedure will be performed, just before the procedure is to be started. The "time-out" may involve the entire surgical team, who must use active communication, and may be briefly documented, such as by using a checklist. The Universal Protocol includes, at the least, verification of the correct patient identity, the correct side and site, an agreement on the procedure to be done, the correct patient position and the availability of correct implants and any special equipment or special requirements.

Figure 4:
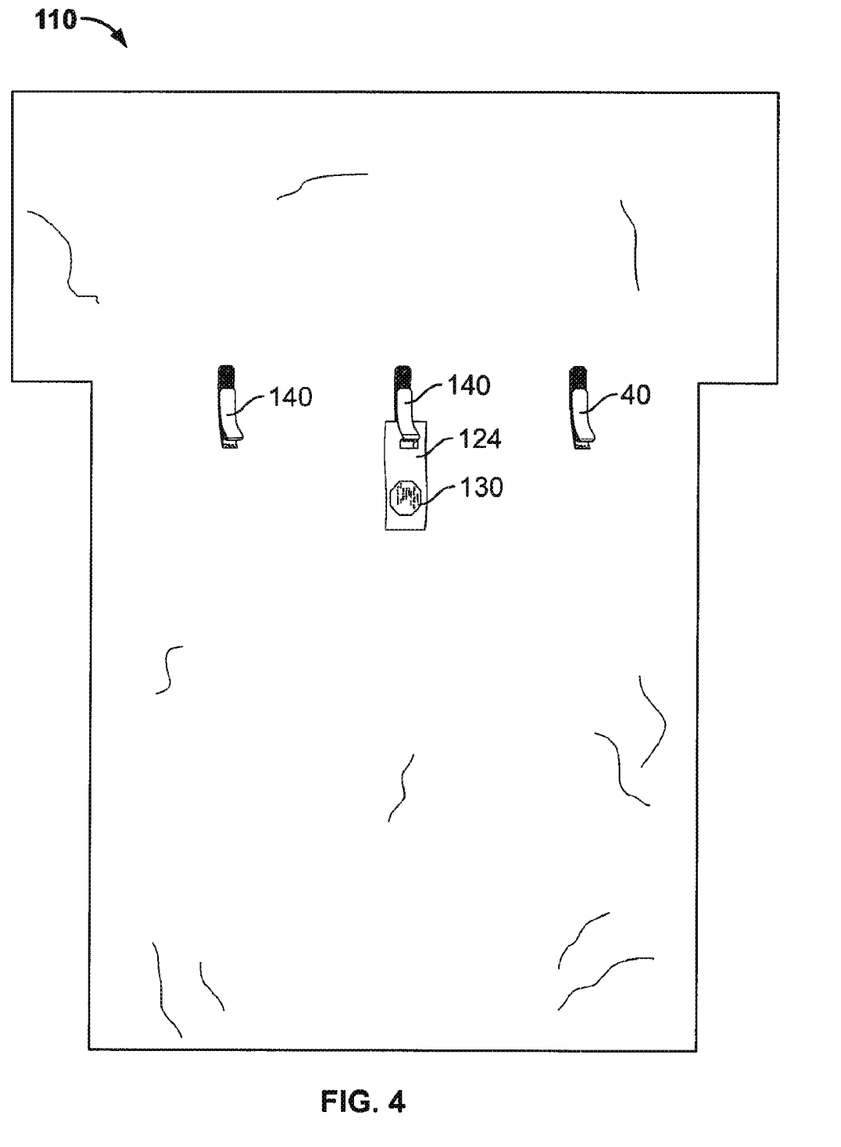
FIG. 4 is a top view of a surgical drape having holders according to another embodiment.

In other embodiments for providing a predetermined verification procedure prior to the start of a surgical procedure, a carrier paper 124 may be attached to the drape via one or more holders 140 that are attached to the surgical drape 110, as shown in FIG. 4. The carrier paper 124 may include an item 130 having a predetermined verification procedure removably attached thereto or printed thereon. The carrier paper 124 may include paper, cloth, plastic, and other materials, i.e., woven and nonwoven materials, and may include a hole for receiving the holder 140. This embodiment provides alternatives for drapes that may not have a fenestration, such as an extremity or split drape.

The holders 140 may include hook and loop fasteners, e.g., Velcro®, strings, loops, ties, adhesives, or other suitable material. The holder 140 may be placed through the hole in the carrier paper 124 and then the holder 140 may be "closed" via the fasteners described herein. Several holders 140 may be attached at different locations on the surgical drape 110 for holding the carrier paper 124 and the item 130. This particular embodiment provides a reminder to the surgical staff to perform the verification procedure and allows them to provide confirmation by properly marking the item 130 and removing it for placement in the patient's medical records.

Other types of holders that may be attached to a surgical drape may also provide a means for attaching a carrier paper having an item with a predetermined verification procedure attached thereto or printed thereon. For example, line holders (not shown) that may be used to loop suction tubing and cautery cords may at times be used to attach a carrier paper to the surgical drape. As with the carrier paper described above, the item having a predetermined verification procedure attached thereto or printed thereon acts as a reminder to the surgical staff to perform the verification procedure prior to starting the surgical procedure.

Figure 5:
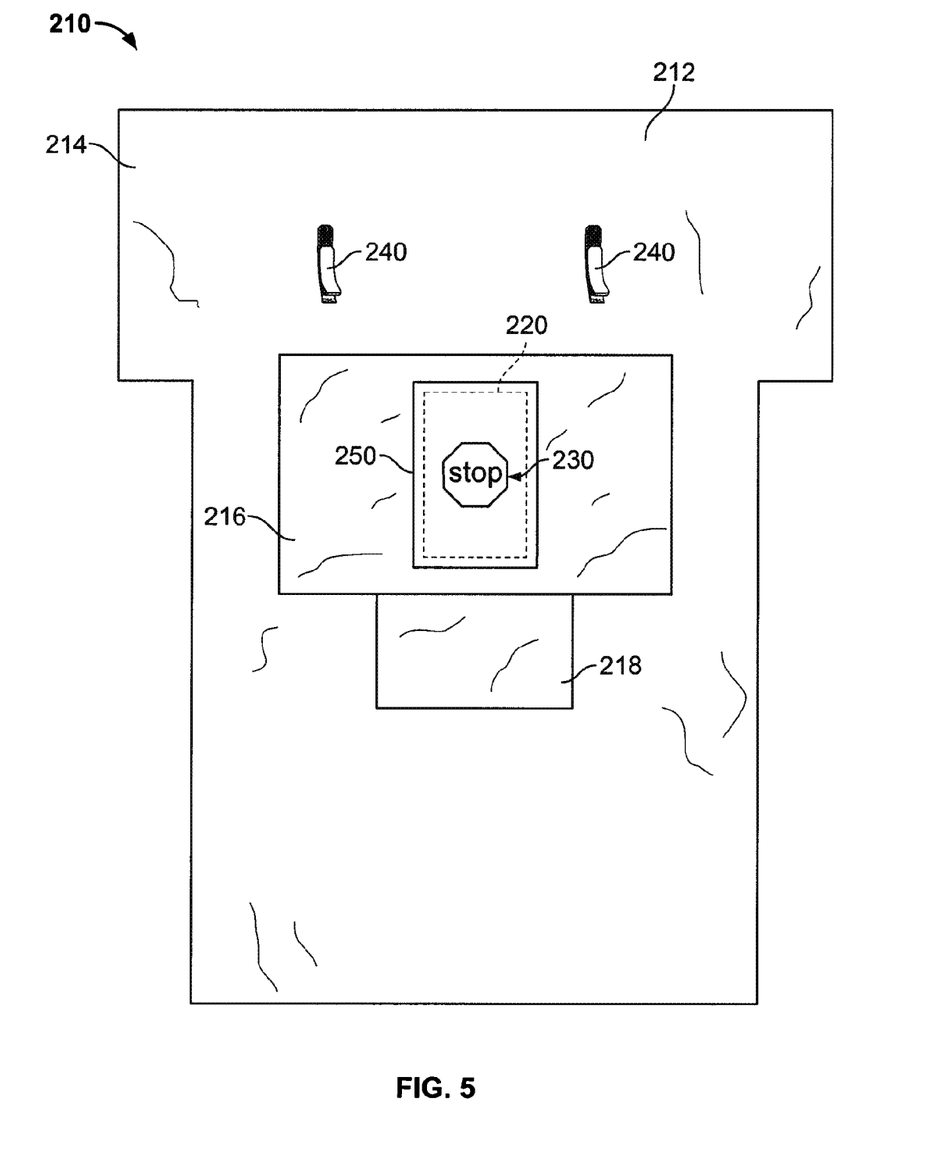
FIG. 5 is a top view of a surgical drape having a fenestration cover according to a further embodiment.

Further embodiments of the present disclosure may include a fenestration cover 250 for covering the fenestration 220 of the surgical drape 210, as shown in FIG. 5. The fenestration cover 250 may include a carrier paper, cloth, plastic, and other materials, i.e., woven and nonwoven materials, that cover the fenestration 220 and may be removed from covering the fenestration 220 upon the completion of a predetermined verification procedure. The fenestration cover 250 may be larger than the area of the fenestration 220 such that the fenestration cover 250 covers the entire area of the fenestration 220. In other embodiments, the fenestration cover 250 may cover a portion of the fenestration 220. The fenestration cover 250 may be attached to the surgical drape 210 according to the methods described herein or may overlay the fenestration 220 without being attached to the surgical drape 210.

As with the barrier 24 and carriers 124, 224 described with respect to FIGS. 1-4, the fenestration cover 250 may include an item 230 removably attached to the fenestration cover 250. The item 230 may include a label, a decal, a sticker, a stamp, an embossment, a tattoo, an ink or screen printed article, any combinations thereof and any other suitable articles that have areas for displaying information related to a predetermined verification procedure. In other embodiments, the fenestration cover 250 may include the predetermined verification procedure printed on the cover 250 itself. For example, the item 230 or cover 250 may include the word "STOP" to indicate that a time-out or pause should be taken so that the verification procedure may be performed. As with the examples described herein, the item 230 or cover 250 may list the elements of the predetermined verification procedure that must be verified before the surgical procedure may begin.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention.

What is claimed is:

1. A surgical drape system for use in a medical procedure, the surgical drape system comprising:
   a surgical drape defining a fenestration configured to be placed over at least a portion of a surgical site of a patient;
   a barrier including a strip of material removably attached to the surgical drape, the barrier extending over and obstructing at least a portion of the fenestration thereby preventing the start of the surgical procedure prior to removal of the barrier, the strip of material extending from a first side to a second side of the fenestration such that multiple portions of the fenestration remain unobstructed by the barrier is attached to the surgical drape;
   at least one holder attached to the surgical drape; and
   an item held by the holder, the item being associated with a predetermined verification procedure.

2. The surgical drape system of claim 1, wherein the strip of material is adhered to the first and second sides of the fenestration.

3. The surgical drape system of claim 1, wherein the barrier is removed from the surgical drape in accordance with the predetermined verification procedure.

4. The surgical drape system of claim 3, wherein the predetermined verification procedure includes confirmation of a set of conditions prior to the start of the surgical procedure.

5. The surgical drape system of claim 4, wherein the set of conditions includes confirming a correct surgical site, confirming a correct surgical procedure, confirming a correct patient, or confirming a correct side of the patient, or any combination thereof.

6. The surgical drape system of claim 1, wherein the predetermined verification procedure is printed on the item.

7. The surgical drape system of claim 1, wherein the item is removable from the at least one holder and configured to be placed in a patient medical record.

8. The surgical drape system of claim 1, wherein the item includes a label, a sticker, a decal, a stamp, an embossment, a tattoo, an ink-printed article, or a screen-printed article, or any combination thereof.

9. The surgical drape system of claim 1, wherein the predetermined verification procedure is placed on the barrier.

10. The surgical drape system of claim 1, wherein the barrier is configured to be removed completely from the surgical drape such that the fenestration is left completely unobstructed by the barrier.

11. A method of using a surgical drape system to prevent a surgery from prematurely beginning, the method comprising:
    placing a surgical drape over at least a portion of a patient, the surgical drape having a fenestration configured to be placed over at least a portion of a surgical site on the patient, the surgical drape including a removable barrier extending over and obstructing at least a portion of the fenestration thereby preventing the start of a surgical procedure, the removable barrier extending from a first side to a second side of the fenestration such that multiple portions of the fenestration remain unobstructed by the removable barrier while the barrier is attached to the surgical drape, the surgical drape having at least one holder bearing an item associated with a predetermined verification procedure including a set of predetermined conditions;
    verifying the set of predetermined conditions prior to removing the barrier; and
    removing the barrier prior to beginning the surgical procedure.

12. The method of claim 11, wherein verifying the set of predetermined conditions includes confirming a correct surgical site, a correct surgical procedure, a correct patient, or a correct side of the patient, or any combination thereof.

13. The method of claim 11, further comprising indicating on the item that the set of predetermined conditions is verified.

14. The method of claim 11, further comprising removing the item associated with the barrier and placing the item in a patient medical record.

15. A surgical drape for use in a medical procedure, the surgical drape comprising:
    a base having a top surface and a bottom surface;
    a fenestration defined through a portion of the base;
    a removable barrier attached to the base, the barrier extending over and obstructing at least a portion of the fenestration to thereby prevent commencement of the medical procedure, the removable barrier extending from a first side to a second side of the fenestration such that multiple portions of the fenestration remain unobstructed by the removable barrier while the barrier is attached to the surgical drape, whereby removing the barrier from the base leaves the fenestration unobstructed by the barrier and thereby allows for commencement of the surgical procedure; and
    at least one holder attached to the top surface of the base, the holder holding an item associated with a predetermined verification procedure.

16. The surgical drape of claim 15, further comprising an indicator attached to the barrier, the indicator being configured to indicate that a predetermined verification procedure has been conducted.

17. The surgical drape of claim 16, wherein the indicator is selectively removable from the barrier.

18. The surgical drape of claim 15, wherein the barrier includes a plurality of perforations, the barrier being removable from the base by tearing the barrier along the plurality of perforations.

19. The surgical drape of claim 15, wherein the barrier is attached to the base via one or more attachment strips.

20. The surgical drape of claim 15, wherein the predetermined verification procedure includes verification of at least a correct patient, a correct surgical procedure, and a correct surgical site.

* * * * *